(12) United States Patent
van der Weide et al.

(10) Patent No.: US 11,135,034 B2
(45) Date of Patent: *Oct. 5, 2021

(54) SIGNAL TAG DETECTION COMPONENTS, DEVICES, AND SYSTEMS

(71) Applicant: Elucent Medical, Inc., Eden Prairie, MN (US)

(72) Inventors: Daniel W. van der Weide, Madison, WI (US); Fred T. Lee, Jr., Madison, WI (US); Robert C. Stewart, Mancos, CO (US); Lee G. Wilke, Madison, WI (US)

(73) Assignee: Elucent Medical, Inc., Eden Prairie, MN (US)

( * ) Notice: Subject to any disclaimer, the term of this patent is extended or adjusted under 35 U.S.C. 154(b) by 102 days.

This patent is subject to a terminal disclaimer.

(21) Appl. No.: 16/356,174

(22) Filed: Mar. 18, 2019

(65) Prior Publication Data

US 2019/0239980 A1 Aug. 8, 2019

Related U.S. Application Data

(60) Continuation of application No. 15/645,414, filed on Jul. 10, 2017, now Pat. No. 10,245,118, which is a
(Continued)

(51) Int. Cl.
*A61B 5/05* (2021.01)
*A61B 90/00* (2016.01)
(Continued)

(52) U.S. Cl.
CPC .......... *A61B 90/39* (2016.02); *A61B 18/1402* (2013.01); *A61B 90/98* (2016.02);
(Continued)

(58) Field of Classification Search
CPC ...... A61B 18/1402; A61B 2017/00115; A61B 2017/00199; A61B 2018/00904;
(Continued)

(56) References Cited

U.S. PATENT DOCUMENTS 3,689,885 A 9/1972 Kaplan et al.
3,706,094 A 12/1972 Cole et al.
(Continued)

FOREIGN PATENT DOCUMENTS

CN 101069640 11/2007
CN 102264292 11/2011
(Continued)

OTHER PUBLICATIONS

International Search Report and Written Opinion for PCT/US2019/035424, dated Oct. 24, 2019, 13 pages.
(Continued)

*Primary Examiner* — Christine H Matthews
(74) *Attorney, Agent, or Firm* — Casimir Jones, S.C.; Brian F. Bradley

(57) ABSTRACT

Provided herein are systems, devices, assemblies, and methods for localization of a tag in a tissue of a patient. For example, provided herein are systems, devices, and methods employing a detection component that is attached to or integrated with a surgical device, where the detection component detects a signal from a tag in a patient, where the tag is activated by remote introduction of a magnetic field.

6 Claims, 8 Drawing Sheets

Related U.S. Application Data division of application No. 14/992,443, filed on Jan. 11, 2016, now Pat. No. 9,730,764.

(60) Provisional application No. 62/236,660, filed on Oct. 2, 2015.

(51) Int. Cl.
*A61B 90/98* (2016.01)
*A61B 18/14* (2006.01)
*A61B 17/00* (2006.01)
*A61B 18/00* (2006.01)
*A61B 34/20* (2016.01)

(52) U.S. Cl.
CPC ..... *A61B 34/20* (2016.02); *A61B 2017/00115* (2013.01); *A61B 2017/00199* (2013.01); *A61B 2018/00904* (2013.01); *A61B 2018/00988* (2013.01); *A61B 2090/3908* (2016.02); *A61B 2090/3945* (2016.02); *A61B 2090/3958* (2016.02); *A61B 2090/3962* (2016.02); *A61B 2562/0223* (2013.01)

(58) Field of Classification Search
CPC .... A61B 2090/3945; A61B 2090/3958; A61B 2562/0223; A61B 34/20; A61B 90/98
See application file for complete search history.

(56) References Cited

U.S. PATENT DOCUMENTS

| | | | |
|---|---|---|---|
| 4,494,545 A | 1/1985 | Slocum et al. |
| 4,561,443 A | 12/1985 | Hogrefe et al. |
| 4,804,054 A | 2/1989 | Howson et al. |
| 5,012,236 A | 4/1991 | Troyk et al. |
| 5,095,309 A | 3/1992 | Troyk et al. |
| 5,142,292 A | 8/1992 | Chang |
| 5,198,807 A | 3/1993 | Troyk et al. |
| 5,221,831 A | 6/1993 | Geiszler et al. |
| 5,241,961 A | 9/1993 | Henry |
| 5,752,513 A | 5/1998 | Acker et al. |
| 5,867,101 A | 2/1999 | Copeland et al. |
| 6,020,856 A | 2/2000 | Alicot |
| 6,026,818 A | 2/2000 | Blair et al. |
| 6,047,214 A | 4/2000 | Mueller et al. |
| 6,053,873 A | 4/2000 | Govari et al. |
| 6,069,564 A | 5/2000 | Hatano et al. |
| 6,198,963 B1 | 3/2001 | Haim et al. |
| 6,249,212 B1 | 6/2001 | Beigel et al. |
| 6,263,247 B1 | 7/2001 | Mueller et al. |
| 6,361,532 B1 | 3/2002 | Burek |
| 6,363,940 B1 | 4/2002 | Krag |
| 6,499,488 B1 | 12/2002 | Hunter et al. |
| 6,675,810 B2 | 1/2004 | Krag |
| 6,698,433 B2 | 3/2004 | Krag |
| 6,765,476 B2 | 7/2004 | Steele et al. |
| 6,784,788 B2 | 8/2004 | Beigel et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,889,833 B2 | 5/2005 | Seiler et al. |
| 6,977,504 B2 | 12/2005 | Wright et al. |
| 7,007,699 B2 | 3/2006 | Martinelli et al. |
| 7,023,391 B2 | 4/2006 | Wuidart et al. |
| 7,026,927 B2 | 4/2006 | Wright et al. |
| 7,135,978 B2 | 11/2006 | Gisselberg et al. |
| 7,174,201 B2 | 2/2007 | Govari et al. |
| 7,176,798 B2 | 2/2007 | Dimmer et al. |
| 7,289,839 B2 | 10/2007 | Dimmer et al. |
| 7,307,530 B2 | 12/2007 | Fabian et al. |
| 7,319,396 B2 | 1/2008 | Homanfar et al. |
| 7,347,379 B2 | 3/2008 | Ward et al. |
| 7,366,562 B2 | 4/2008 | Dukesherer et al. |
| 7,407,054 B2 | 8/2008 | Seiler et al. |
| 7,411,505 B2 | 8/2008 | Smith et al. |
| 7,414,404 B2 | 8/2008 | Keene |
| 7,420,468 B2 | 9/2008 | Fabian et al. |
| 7,474,223 B2 | 1/2009 | Nycz et al. |
| 7,518,518 B2 | 4/2009 | Homanfar et al. |
| 7,549,960 B2 | 6/2009 | Govari |
| 7,558,616 B2 | 7/2009 | Govari et al. |
| 7,575,550 B1 | 8/2009 | Govari |
| 7,590,441 B2 | 9/2009 | Govari et al. |
| 7,632,270 B2 | 12/2009 | Livneh |
| 7,657,301 B2 | 2/2010 | Mate et al. |
| 7,657,302 B2 | 2/2010 | Mate et al. |
| 7,657,303 B2 | 2/2010 | Mate et al. |
| 7,684,849 B2 | 3/2010 | Wright et al. |
| 7,696,876 B2 | 4/2010 | Dimmer et al. |
| 7,715,898 B2 | 5/2010 | Anderson |
| 7,747,307 B2 | 6/2010 | Wright et al. |
| 7,751,865 B2 | 7/2010 | Jascob et al. |
| 7,778,687 B2 | 8/2010 | Dimmer et al. |
| 7,814,916 B2 | 10/2010 | Revie et al. |
| 7,817,040 B2 | 10/2010 | Homanfar et al. |
| 7,818,044 B2 | 10/2010 | Dukesherer et al. |
| 7,840,253 B2 | 11/2010 | Tremblay et al. |
| 7,848,553 B2 | 12/2010 | Hertel et al. |
| 7,871,423 B2 | 1/2011 | Livneh |
| 7,899,513 B2 | 3/2011 | Phillips et al. |
| 7,912,529 B2 | 3/2011 | Herron et al. |
| 7,926,491 B2 | 4/2011 | Wright et al. |
| 7,971,341 B2 | 7/2011 | Dukesherer et al. |
| 7,993,335 B2 | 8/2011 | Rioux et al. |
| 8,011,508 B2 | 9/2011 | Seiler et al. |
| 8,012,154 B2 | 9/2011 | Livneh |
| 8,057,407 B2 | 11/2011 | Martinelli et al. |
| 8,057,468 B2 | 11/2011 | Konesky |
| 8,100,897 B2 | 1/2012 | Zoran |
| 8,113,210 B2 | 2/2012 | Petcavich et al. |
| 8,114,181 B2 | 2/2012 | Gogolin |
| 8,196,589 B2 | 6/2012 | Gisselberg et al. |
| 8,226,640 B2 | 7/2012 | Zoran |
| 8,239,001 B2 | 8/2012 | Verard et al. |
| 8,271,069 B2 | 9/2012 | Jascob et al. |
| 8,354,837 B2 | 1/2013 | Anderson |
| 8,359,730 B2 | 1/2013 | Burg et al. |
| 8,377,388 B2 | 2/2013 | Konesky |
| 8,399,837 B2 | 3/2013 | Robbins et al. |
| 8,409,190 B2 | 4/2013 | Konesky et al. |
| 8,467,852 B2 | 6/2013 | Csavoy et al. |
| 8,549,732 B2 | 10/2013 | Burg et al. |
| 8,628,524 B2 | 1/2014 | Shilev |
| 8,644,907 B2 | 2/2014 | Hartmann et al. |
| 8,647,342 B2 | 2/2014 | Livneh |
| 8,696,663 B2 | 4/2014 | Pardoll et al. |
| 8,728,076 B2 | 5/2014 | Livneh |
| 8,795,265 B2 | 8/2014 | Konesky et al. |
| 8,795,272 B2 | 8/2014 | Rioux et al. |
| 8,802,022 B2 | 8/2014 | Konesky |
| 8,830,037 B2 | 9/2014 | Burke et al. |
| 8,857,043 B2 | 10/2014 | Dimmer et al. |
| 8,892,185 B2 | 11/2014 | Chi Sing et al. |
| 8,939,153 B1 | 1/2015 | Reicher et al. |
| 8,948,845 B2 | 2/2015 | Glossop et al. |
| 8,968,171 B2 | 3/2015 | McKenna et al. |
| 8,973,584 B2 | 3/2015 | Brander et al. |
| 8,979,834 B2 | 3/2015 | Zoran et al. |
| 8,998,899 B2 | 4/2015 | Shilev et al. |
| 9,002,434 B2 | 4/2015 | Uchiyama et al. |
| 9,060,765 B2 | 6/2015 | Rencher et al. |
| 9,095,333 B2 | 8/2015 | Konesky et al. |
| 9,144,453 B2 | 9/2015 | Rencher et al. |
| 9,234,877 B2 | 1/2016 | Hattersley et al. |
| 9,239,314 B2 | 1/2016 | Hattersley et al. |
| 9,730,764 B2 | 8/2017 | Van Der Weide et al. |
| 9,987,097 B2 | 6/2018 | Van Der Weide et al. |
| 10,154,799 B2 | 12/2018 | Van Der Weide et al. |
| 10,245,118 B2 | 4/2019 | Van Der Weide et al. |
| 10,245,119 B2 | 4/2019 | Van Der Weide et al. |
| 10,278,779 B1 | 5/2019 | Rudie et al. |
| 2003/0018246 A1 | 1/2003 | Govari et al. |
| 2003/0117269 A1 | 6/2003 | Dimmer |

(56) References Cited

U.S. PATENT DOCUMENTS

| | | |
|---|---|---|
| 2003/0153850 A1 | 8/2003 | Davis et al. |
| 2004/0093187 A1 | 5/2004 | Dames et al. |
| 2004/0123871 A1 | 7/2004 | Wright et al. |
| 2004/0169505 A1 | 9/2004 | Alun et al. |
| 2004/0199067 A1 | 10/2004 | Bock et al. |
| 2006/0093089 A1 | 5/2006 | Vertatschitsch et al. |
| 2007/0135803 A1 | 6/2007 | Belson |
| 2007/0232882 A1 | 10/2007 | Glossop et al. |
| 2008/0125630 A1 | 5/2008 | Caylor |
| 2008/0132860 A1 | 6/2008 | Smith et al. |
| 2008/0194912 A1 | 8/2008 | Trovato et al. |
| 2008/0213382 A1 | 9/2008 | Ivkov et al. |
| 2008/0281190 A1 | 11/2008 | Petcavich et al. |
| 2009/0009335 A1 | 1/2009 | Stewart et al. |
| 2009/0281419 A1 | 11/2009 | Troesken et al. |
| 2010/0004523 A1 | 1/2010 | August et al. |
| 2010/0274145 A1 | 10/2010 | Tupin et al. |
| 2010/0275934 A1 | 11/2010 | Keren |
| 2010/0305430 A1 | 12/2010 | Troesken et al. |
| 2011/0152673 A1 | 6/2011 | Doerr et al. |
| 2011/0152677 A1 | 6/2011 | Faul |
| 2011/0201923 A1 | 8/2011 | Shen |
| 2011/0278948 A1 | 11/2011 | Forsell |
| 2012/0082342 A1 | 4/2012 | Kim et al. |
| 2013/0052953 A1 | 2/2013 | Rofougaran |
| 2013/0237982 A1 | 9/2013 | Rencher et al. |
| 2013/0345561 A1 | 12/2013 | Quigley |
| 2014/0018663 A1 | 1/2014 | Harmer et al. |
| 2014/0062717 A1 | 3/2014 | Mudumbai et al. |
| 2014/0066754 A1 | 3/2014 | Chi Sing et al. |
| 2014/0148692 A1 | 5/2014 | Hartmann et al. |
| 2014/0309522 A1 | 10/2014 | Fullerton et al. |
| 2015/0100109 A1 | 4/2015 | Feldman et al. |
| 2015/0129664 A1 | 5/2015 | Brar |
| 2015/0141811 A1 | 5/2015 | Ritchey et al. |
| 2015/0196369 A1 | 7/2015 | Glossop et al. |
| 2015/0264891 A1 | 9/2015 | Brander et al. |
| 2016/0022216 A1 | 1/2016 | Goldshtein et al. |
| 2016/0051164 A1 | 2/2016 | Derichs et al. |
| 2016/0192960 A1 | 7/2016 | Bueno et al. |
| 2017/0007352 A1 | 1/2017 | Van Der Weide et al. |
| 2017/0095313 A1 | 4/2017 | Van Der Weide et al. |
| 2017/0095315 A1 | 4/2017 | Van Der Weide et al. |
| 2017/0238996 A1 | 8/2017 | Frame et al. |
| 2017/0312046 A1 | 11/2017 | Van Der Weide et al. |
| 2018/0353259 A1 | 12/2018 | Van Der Weide et al. |
| 2019/0090779 A1 | 3/2019 | Van Der Weide et al. |
| 2019/0209263 A1 | 7/2019 | Van Der Weide et al. |
| 2019/0365478 A1 | 12/2019 | Rudie et al. |
| 2019/0388178 A1 | 12/2019 | Rudie et al. |

FOREIGN PATENT DOCUMENTS

| | | |
|---|---|---|
| DE | 10112303 | 10/2002 |
| DE | 102011006537 | 10/2012 |
| EP | 1232730 | 8/2002 |
| JP | 2012-524627 | 10/2012 |
| WO | WO 1993/005707 | 4/1993 |
| WO | WO 2007/064013 | 6/2007 |
| WO | WO 2010/058150 | 5/2010 |
| WO | WO 2010/124117 | 10/2010 |
| WO | WO 2015039039 | 3/2015 |
| WO | WO 2015/063280 | 5/2015 |
| WO | WO 2015112863 | 1/2016 |
| WO | WO 2017059228 | 4/2017 |
| WO | WO 2018/031826 | 2/2018 |
| WO | WO 2019/236600 | 12/2019 |

OTHER PUBLICATIONS

European Search Report for EP17840310.1, dated Mar. 30, 2020, 11 pages.
European Supplemental Search Report for EP16852699.4, dated May 10, 2019, 10 pages.
Li et al., Radio frequency identification technology: applications, technical challenges and strategies, Management Department Journal Article, 2006, paper 34, 28 pages.
Luini et al., Comparison of Radioguided excision with wire localization of occult breast lesions, Br. J. Surg, 1999, 86:522-525.
Mickle et al., Intellecutual Property and Ubiquitos RFID, Recent Patents on Electrical Engineering, 2008, 1:59-67.
Radio Frequency Identification: Opportunites and Challenges in Immpementation, Department of Commerce, 2005, Washington D.C., 38 pages.
Shah et al, Expanding the use of real-time electromagnetic tracking in radiation oncology, J Appl Clin Med Phys. Nov. 15, 2011; 12(4):3590.
Shantz, A Near Field Propagation Law & a Novel Fundamental Limit to Antenna Gain Versus Size. Antennas and Propagation Society International Symposium, 2005 IEEE, Jul. 3-8, 2005, Washington D.C. 4 pages.
Soon, Radio Frequency Identification History and Development, Chapt. 1, Ubiquitous and Pervasive Computing: Concepts, Methodologies, Tools, and Applications, 2010, ed. Symonds, 17 pages.
Stockman, Communication by Means of Reflected Power, Proceedings of the I.R.E., 1948, 36(10):1196-1204.
Takahata et al., Thoracoscopic surgery support system using passive RFID marker, 34th Annual International Conference of the IEEE EMBS, San Diego, CA, Aug. 28-Sep. 1, 2012, pp. 183-186.
Van Lieshout et al., RFID Technologies: Emerging Issues, Challenges and Policy Options, JRC Scientific and Technical Reports, 2007, 278 pages.
Want, RFID: A Key to Automating Everything, Scientific American, Inc., Jan. 2004, pp. 56-63.
International Search Report and Written Opinion, dated May 5, 2016, for PCT/US2015/012687, 11 pages.
International Search Report and Written Opinion for PCT/US2016/054738, dated Jan. 31, 2017, 9 pages.
European Supplemental Search Report for EP15740262.9, dated Sep. 18, 2017, 14 pages.
International Search Report and Written Opinion for PCT/US2017/046379, dated Dec. 5, 2017, 15 pages.

21

SIGNAL TAG DETECTION COMPONENTS, DEVICES, AND SYSTEMS

The present application is a continuation of U.S. patent application Ser. No. 15/645,414, filed Jul. 10, 2017, now allowed, which is a divisional of U.S. patent application Ser. No. 14/992,443, filed Jan. 11, 2016, now U.S. Pat. No. 9,730,764, which claims priority to U.S. Provisional Application Ser. No. 62/236,660, filed Oct. 2, 2015, each of which are herein incorporated by reference in its entirety.

FIELD

Provided herein are systems, devices, assemblies, and methods for localization of a tag in a tissue of a patient. For example, provided herein are systems, devices, and methods employing a detection component that is attached to or integrated with a surgical device, where the detection component detects a signal from a tag in a patient, where the tag is preferably activated by remote introduction of a magnetic field.

BACKGROUND

A common and serious challenge for many medical procedures is the accurate localization of treatment areas. For example, the location of lesions, such as tumors that are to undergo treatment, including surgical resection, continues to present a challenge to the medical community. Existing systems are expensive, complex, time-consuming, and often unpleasant for the patient. Such issues are illustrated by the surgical treatment of breast lesions.

A common technique used in breast tumor surgery is wire localization of the lesions. Precise preoperative localization of some breast lesions is necessary before removal of the lesion. Wire localization is used to mark the location of a breast abnormality. The procedure ensures greater accuracy for a breast biopsy or lumpectomy. The surgeon typically uses the wire as a guide to the tissue that needs to be removed. Wire localization is typically conducted in the radiology department of the hospital or surgical center. Mammograms (or in some cases, ultrasound images) are taken to show the location of the breast abnormality. Patients are awake during the placement of the wire, but the breast tissue is numbed to reduce or avoid pain from the needle or the wire. It is possible to feel pressure or pulling sensations during the wire placement. Once images have been taken, and the tissue has been numbed, the radiologist will use a needle to target the breast abnormality. The tip of this needle rests in the location that the surgeon needs to find in order to remove the right tissue. A slender wire is threaded down through the needle and out of its tip, to lodge at the target tissue. The needle is removed, leaving the wire in place. With the wire in place, the patient has another mammogram, to check that the tip of the wire is properly positioned. If the wire is not in the correct place, the radiologist will reposition and re-check it, to ensure accurate placement. When the wire is finally positioned, it will be secured in place with tape or a bandage. The wire localization procedure can take about an hour, and is usually scheduled hours before biopsy or lumpectomy. Thus, the patient must often wait hours for surgery with the wire present in their body and protruding from their skin. The wire is removed, along with some breast tissue, during surgery. This process takes many hours, involves multiple imaging steps, and is inconvenient and unpleasant for the patient—as well as being expensive.

A similar type of procedure is done to localize pulmonary nodules prior to resection. In some cases where pulmonary nodules may be difficult to locate at conventional open surgery or at thoracoscopy, a hook wire, injection of visible dye, or a radionuclide is placed in or around the nodule in an attempt to improve localization prior to removal. This procedure usually takes place in the CT suite prior to the removal of the nodule. The patient is then transported to the surgical unit and the surgeon cuts down on the wire, uses a radionuclide detector, or uses visual landmarks to localize and remove the nodule.

In other types of surgeries and medical procedures, physicians may have trouble locating a target prior to removal or manipulation. Examples of this include the removal of masses, fluid collections, foreign bodies or diseased tissues. Other times, placements of catheters or other percutaneous procedures are performed either without direct visualization or with the lack of a specific guidance modality. Performing procedures without precise guidance can increase the amount of damage to normal tissues and decrease the patient's functional status.

Percutaneous biopsy is a well-accepted, safe procedure performed in virtually every hospital. Biopsy often entails placement of a co-axial guide needle through which the biopsy device is placed into the target. Many of the lesions that are removed, punctured or manipulated as described above have previously undergone successful percutaneous biopsy. The placement of the guide needle for biopsy is an opportunity to place a fiduciary or other localizing system without causing additional tissue trauma than the patient would otherwise undergo.

Many other medical devices and procedures could benefit from improved tissue localization. These include any procedure or test that is degraded by any bodily motion such as cardiac motion, respiratory motion, motion produced by the musculoskeletal system, or gastrointestinal/genitourinary motion. Examples of these include external beam radiation therapy, placement of brachytherapy seeds, imaging tests including but not limited to CT, MRI, fluoroscopy, ultrasound, and nuclear medicine, biopsies performed in any fashion, endoscopy, laparoscopic and thoracoscopic surgery and open surgical procedures.

Improved systems and methods are needed for tissue localization for medical procedures.

SUMMARY

Provided herein are systems, devices, assemblies, and methods for localization of a tag in a tissue of a patient. For example, provided herein are systems, devices, and methods employing a detection component that is attached to or integrated with a surgical device, where the detection component detects a signal from a tag in a patient, where the tag is activated by remote introduction of a magnetic field. In certain embodiments, the detection component comprises three or more sense coils to triangulate a tag location and the distance of the tag from the detection component.

In some embodiments, provided herein are methods for localizing a tissue region of a patient, comprising: a) placing a remote activating device and a patient in proximity to each other, wherein the remote activating device is able to generate a magnetic field, and wherein a tag is located in a tissue of the patient; and b) localizing the tag in the patient by generating a magnetic field with the remote activating device and detecting a signal from the tag using a detector component, wherein the detector component comprises at least one sense coil and is attached to, or integrated with, a surgical device, and wherein the detector component and remote activating device are separate (e.g., not attached to, or part of, each other).

In certain embodiments, the at least one sense coil comprises three sense coils that are separated from each other by at least 10 mm (e.g., at least 10 . . . 15 . . . 20 . . . 25 . . . 30 . . . 40 . . . 50 . . . 60 . . . 70 . . . 100 . . . 125 . . . 150 . . . 175 . . . or 200 mm). In other embodiments, the at least one sense coil comprises three sense coils arranged in a triangle. In particular embodiments, the triangle is an equilateral triangle or approximately an equilateral triangle.

In particular embodiments, the detector component comprises a housing with a device-securing component (e.g., an opening in the housing; a snap; tongue and groove; slot; magnetic attachment; etc). In some embodiments, the surgical device is in inserted through the device-securing opening such that the housing surrounds a portion of the surgical device (and such that said surgical device is secured to said detection component).

In certain embodiments, the remote activating device, the detector component, and the surgical device are electrically-linked and/or wirelessly linked to a control unit, wherein the control unit comprises a processor and control software. In further embodiments, the detection component comprises a display (e.g., visual, audible, etc.), and wherein the control unit processes signals from the detection component and provides data that is displayable on the display. In particular embodiments, the surgical device comprises an electrical surgical device that is turned on and off by a user, wherein the control unit allows the remote activating device to generate the magnetic field when the electrical surgical device is off, and prevents the remote activating device from generating the magnetic field when the electrical surgical device is on (e.g., ensuring that the surgical device and detection system do not interfere with one another). In other embodiments, the surgical device comprises a power cord, wherein an AC current clamp is attached to the power cord, wherein the AC current clamp is electrically-linked or wirelessly linked to the control unit, wherein the AC current clamp senses when the electrical surgical device is on or off and reports this to the control unit (e.g., such that the control unit can ensure that the magnetic field from the surgical device and from the remote activating device are not active at the same time).

In certain embodiments, the control, unit and/or detection component, has information stored thereon that helps guide the information displayed on the detection component. For example, the information may include data on the type of medical device the detection component is attached to, or what tip or cutting implement is being used with a particular medical device. In this regard, the precise location of the cutting tip of a medical device and it's relation to the tag (e.g., distance to the tag) can be communicated to the surgeon (e.g., for very precise instructions on cutting tissue). Such information can, for example, be manually entered into the control unit or detection component by the user, or automatically found (e.g., by a barcode or other indicator) when a detection component is attached to a particular medical device.

In certain embodiments, the surgical device comprises an electrocautery device, a laser cutting device, a plasma cutting device, or a metal cutting device (e.g., a surgical device manufactured by BOVIE MEDICAL). Additional examples of medical devices that could be attached to, or integrated with, the detection components of the present disclosure are found in the following U.S. Pat. Nos. 9,144,453; 9,095,333; 9,060,765; 8,998,899; 8,979,834; 8,802,022; 8,795,272; 8,795,265; 8,728,076; 8,696,663; 8,647,342; 8,628,524; 8,409,190; 8,377,388; 8,226,640; 8,114,181; 8,100,897; 8,057,468; 8,012,154; 7,993,335; 7,871,423; 7,632,270; 6,361,532; all of which are herein incorporated by reference in their entireties, and particularly with respect to the handheld medical devices disclosed therein. In some embodiments, the remote activating device comprises one or more excitation coils. In further embodiments, the remote activating device comprises a pad, and wherein the pad is placed under the patient or under a bed the patient is on. In other embodiments, the signal is an irregularity (e.g., interruption or perturbation) in the magnetic field caused by the tag. In other embodiments, the tag comprises a metal particle (e.g., a ferrite particle).

In other embodiments, the detector component comprises an electronics component, wherein the electronics component comprises a signal processor. In certain embodiments, the detector component comprises an electronics component, wherein the electronics component comprises: i) a spatial orientation indicator (e.g., visual, audible, etc.), and/or ii) a distance-to-tag indicator (e.g., visual, audible, etc.). In further embodiments, the tissue region is selected from the group consisting of: a lesion, a tumor, a breast tumor, a blood vessel, a lymph node, and sentinel node.

In certain embodiments, the detector component comprises a first display for presenting distance to tag information (e.g., visual, audible, lights, color, vibration, tactile, etc.), a second display for presenting vertical axis orientation, such as a preset preferred angle for approaching a tag in a patient (e.g., a visual, audible, lights, colors, vibration, tactile, etc. display); and/or a third display for presenting horizontal orientation (e.g., left to right information so the surgical device can be centered when approaching the tag). In some embodiments, the detector components comprises a plurality of displays (e.g., visual, audible, sensory, etc.) that allow the correct pitch and yaw axes to be employed (to minimize non-target tissue damage), and/or further a display that provides distance to tag information. In certain embodiments, the detector component is moved around the patient's body prior to surgery to orient the detector component. In certain embodiments, a series of lights and/or sounds are provided on the detector component that guide the surgeon (e.g., the surgeon attempts to keep the lights in a center of an "X" series of lights, and/or to keep the volume of warning sounds off or as low as possible). For example, the detector component may have an array or geometric shape of lights of different colors that can light up informing the user (e.g., doctor) with regard to location of a tag and/or position of the detector component (and corresponding surgical instrument), such that the user does not have to look away from the surgical field or procedure field.

In some embodiments, the signal comprises: i) a signal detectable by sensory perception; ii) an interruption or perturbation in the magnetic field; or iii) light. In further embodiments, the tag comprises: a radio-frequency identification (RFID) chip; ii) a resonant or self-resonant object; or iii) a metal particle. In other embodiments, the tag has a length, width, and depth, wherein the length is less than 10 mm, the width is less than 4 mm, and the depth is less than 4 mm. In other embodiments, the localizing comprises detecting a change based on intensity, frequency, color, or sound of the signal. In certain embodiments, the tag in the tissue of the patient is detected at a depth of at least 1 mm . . . 10 mm . . . 45 mm . . . 95 mm . . . 125 mm . . . 174 mm . . . or 200 mm.

In certain embodiments, the methods further comprise the step of surgically removing a tumor from the patient. In additional embodiments, the methods further comprise the step of administering radiation therapy to the patient using the tag as a fiducial. In other embodiments, the patient comprises a plurality of tags, and wherein the methods further comprise the step of determining locations of the plurality of tags to localize the tissue region in three dimensional space.

In some embodiments, the tip of the localizing device (e.g., such as a surgical instrument or an electrocautery system) is placed in a specific location (e.g., a jig containing a tag at a known distance and orientation from the tip) for calibration. This may require, for example, entering data into the system to describe the length or shape of the instrument.

In some embodiments, provided herein are systems comprising: a) a detector component comprising a housing and at least one sense coil inside the housing, wherein the detector component detects a signal from a tag inside a patient; and b) a second component selected from the group consisting of: i) a surgical instrument, ii) a remote activating device which generates a magnetic field, iii) a tag that is insertable at a location in a tissue of a patient, and iv) a control unit comprising a processor and a control software, wherein the control unit, when electrically or wirelessly linked to the detector component, provides data to the detector component.

In certain embodiments, the at least one sense coil comprises three sense coils that are separated from each other by at least 10 mm (e.g., at least 10 . . . 25 . . . 45 . . . 55 . . . 75 . . . 137 . . . 168 . . . or 200 mm). In other embodiments, the at least one sense coil comprises at least three sense coils arranged in a triangle. In particular embodiments, the triangle is an equilateral triangle or approximately an equilateral triangle. In certain embodiments, the housing has a device-securing component (e.g., opening in housing; slot; snap; etc.). In other embodiments, the second component comprises the surgical device, and wherein the surgical device is in inserted through the device-securing opening such that the housing surrounds a portion of the surgical device and the surgical device is secured to the housing. In certain embodiments, the surgical instrument comprises a hand-held surgical instrument.

In particular embodiments, the tag generates the signal when exposed to the magnetic field. In further embodiments, the signal is an irregularity in the magnetic field. In other embodiments, the detection component further comprises a display (e.g., visual, audible, tactile, etc.), and wherein the control unit processes signals from the detection component and provides the data that is displayable on the visual display. In other embodiments, the data comprises distance to tag data and/or orientation data. In some embodiments, wherein the control unit, when electrically or wirelessly linked to the detector component and the remote activating component, causes the remote activating device to generate the magnetic field when the electrical surgical device is off, and prevents the remote activating device from generating the magnetic field when the electrical surgical device is on. In other embodiments, the surgical device comprises a power cord, wherein an AC current clamp is attached to the power cord.

In some embodiments, the surgical device comprises an electrocautery device, a laser cutting device, a plasma cutting device, or a metal cutting device. In other embodiments, the remote activating device comprises an excitation coil. In some embodiments, the remote activating device comprises a pad or other generally flat component.

In certain embodiments, the tag comprises a metal particle (e.g., ferrite particle). In some embodiments, the detector component comprises an electronics component, wherein the electronics component comprises a signal processor. In some embodiments, the detector component comprises an electronics component, wherein the electronics component comprises: i) a visual spatial orientation indicator, and/or ii) a distance-to-tag indicator. In certain embodiments, the tag has a length, width, and depth, wherein the length is less than 10 mm, the width is less than 4 mm, and the depth is less than 4 mm.

In some embodiments, provided herein are detector components comprising: i) a housing having a device-securing component (e.g., opening in housing; snap; slot; etc.); and ii) at least one sense coil inside the housing, wherein the detector component detects a signal from a tag inside a patient. In further embodiments, the at least one sense coil comprises three sense coils that are separated from each other by at least 10 mm (e.g., 10 mm . . . 50 . . . 200 mm). In certain embodiments, the at least one sense coil comprises at least three sense coils (e.g., arranged in a triangle, or otherwise able to triangulate the position and distance of tag). In other embodiments, the triangle is an equilateral triangle or approximately an equilateral triangle. In further embodiments, the detector component further comprises an electronics component, wherein the electronics component comprises a signal processor. In other embodiments, the detector component further comprises an electronics component, wherein the electronics component comprises: i) a spatial orientation indicator, and/or ii) a distance-to-tag indicator.

In certain embodiments, provided herein are detector components comprising: i) a housing; and ii) at least three sense coils inside the housing (e.g., arranged in a triangle or otherwise able to triangulate the position and distance of the tag) wherein the detector component is able to detect a signal from a tag inside a patient. In some embodiments, the three sense coils that are separated from each other by at least 10 mm (e.g., 10 mm . . . 100 mm . . . 200 mm). In other embodiments, the triangle is an equilateral triangle or approximately an equilateral triangle. In additional embodiments, the detector component further comprises an electronics component, wherein the electronics component comprises a signal processor. In certain embodiments, the detector component further comprises an electronics component, wherein the electronics component comprises: i) a spatial orientation indicator, and/or ii) a distance-to-tag indicator. In some embodiments, the housing has a device-securing opening therein.

In particular embodiments, provided herein are devices comprising: a) a hand-held surgical instrument, and b) a detector component attached to, or integrated with, the hand-held surgical instrument, wherein the detector component comprises a housing and at least one sense coil inside the housing, wherein the detector component is able to detect an irregularity in a magnetic field.

In some embodiments, the at least one sense coil comprises three sense coils that are separated from each other by at least 10 mm . . . 30 mm . . . 50 mm . . . or 200 mm. In other embodiments, the at least one sense coil comprises three sense coils arranged in a triangle or other arrangement able to triangulate the location of a tag in a patient. In certain embodiments, the triangle is an equilateral triangle or approximately an equilateral triangle. In other embodiments, the detector component comprises a housing with a device-securing component (e.g., opening therein, snap, slot, or other connector) and wherein the surgical device is attached to the detection component via the device-securing component (e.g., surgical device is in inserted through the opening such that the housing surrounds a portion of the surgical device). In other embodiments, the hand-held surgical instrument comprises an electrocautery device, a laser cutting device, a plasma cutting device, or a metal cutting device. In additional embodiments, the hand-held surgical instrument comprises a power cord, and wherein an AC current clamp is attached to the power cord. In other embodiments, the detector component comprises an electronics component, wherein the electronics component comprises a signal processor. In further embodiments, the detector component comprises an electronics component, wherein the electronics component comprises: i) a spatial orientation indicator (e.g., display), and/or ii) a distance-to-tag indicator.

In some embodiments, the tag comprises a self-resonant object (e.g., a small ferrite core with a wound inductor). The wound inductor possesses inter-winding capacitance that in combination with the inductance produces a high frequency resonant circuit. In some embodiments, the tag comprises a resonant object (e.g., self-resonant object is equipped with a chip capacitor to produce resonance at a prescribed frequency). In some embodiments, the tag comprises a resonant or self-resonant object with a diode. A diode in combination with LC circuit produces a sub-harmonic frequency when immersed in a magnetic field of sufficient strength (imposed voltage exceeds the diode's band-gap potential). In some embodiments, the tag comprises a resonant object or self-resonant object with an active modulator (e.g., integrated circuit amplitude modulates resonant circuit). Detection occurs similar to a full duplex (FDX) radio frequency identification (RFID) except that the modulation pattern is a simple sub-harmonic rather than a coded binary pattern.

In some embodiments, the tag is configured for single-use. In some such embodiments, a tag can be disabled or deactivated (e.g., like an EAS tag). This is particularly useful where multiple tags are used in a procedure where individual tags are turned off to make detection of other tags easier (e.g., to avoid or reduce interference between multiple tags). In some embodiments, a burst of energy from an external device is used to disable or deactivate a tag. In other embodiments, the tag has an internal control component that, upon receiving instruction from an external device, turns the tag on or off (e.g., the tag stops "talking" temporarily or permanently).

In some embodiments, the tag has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.).

In some embodiments, the tag is contained in a housing. In some embodiments, no housing is employed. In some embodiments, the housing comprises a biocompatible material. In some embodiments, the housing provides a liquid and/or gas resistant barrier separating the signal source from the exterior of the housing. In some embodiments, the housing is small, permitting administration of the tag through a needle, cannula, endoscope, catheter, or other medical device. In some such embodiments, the housing has an exterior length, width, and depth, wherein the length is 30 mm or less (e.g., 20 mm or less, . . . 10 mm or less, . . . 9 mm or less, . . . 8 mm or less, . . . 5 mm or less, . . . 3 mm or less, . . . , etc.), the width is 5 mm or less (e.g., 4 mm or less, . . . 3 mm or less, . . . 2 mm or less, . . . 1 mm or less, . . . 0.5 mm or less, . . . , etc.), and the depth is 5 mm or less (e.g., 4 mm or less, . . . 3 mm or less, . . . 2 mm or less, . . . 1 mm or less, . . . 0.5 mm or less, . . . , etc.). The housing can be of any desired shape. In some embodiments, the housing is cylindrical along the length axis. In some embodiments, the housing is shaped like a grain of rice (e.g., cylindrical with rounded ends). In some embodiments, the housing is shaped like a pillar (e.g., cylindrical with flat ends). In some embodiments, the housing is polygonal along the length axis (e.g., triangular, square, rectangular, trapezoidal, pentagonal, etc., in cross-section). In some embodiments the housing has struts or other fasteners to keep the device in place, avoiding migration in tissue. These struts may deploy upon placement in tissue. In some embodiments the fastener may be a biocompatible material that bonds with surrounding tissue.

In some embodiments, the housing is a single uniform component synthesized around the interior components of the tag. In other embodiments, the housing is made of two or more separate segments that are sealed together after introduction of the interior components of the tag. In some embodiments, the tag is completely or partially covered in a coating. In some embodiments, the coating comprises a biocompatible material (e.g., parylene-C, etc.).

In some embodiments, the tag does not comprise any power source. For example, in some embodiments, the signal is generated from the signal source in response to a magnetic field as the activation event (i.e., electromagnetic induction).

In some embodiments, the tag comprises a radio-frequency identification (RFID) chip (e.g., in a housing). In some embodiments, the RFID chip comprises a radio-frequency electromagnetic field coil that modulates an external magnetic field to transfer a coded identification number and/or other coded information when queried by a reader device. In some embodiments, the RFID chip collects energy from an EM field generated by the activating device (or other device) and then acts as a passive transponder to emit microwaves or UHF radio waves. In some embodiments, a reader (which can be part of the activation device or another device) sends a signal to the RFID chip and reads its response. In some embodiments, the reader is a hand-held device that comprises a computer system RFID software or RFID middleware. In some embodiments, the RFID chip is read-only. In other embodiments, it is read/write. The technology is not limited by the nature of the information provided by the RFID chip. In some embodiments, the information includes a serial number, lot or batch number, time information (e.g., production date; surgery date; etc.); patient-specific information (e.g., name, family history, drugs taken, allergies, risk factors, procedure type, gender, age, etc.); procedure-specific information; etc. The technology is not limited by the frequency used. In some embodiments, the RFID frequency is in the 120-150 kHz band (e.g., 134 kHz), the 13.56 MHz band, the 433 MHz band, the 865-868 MHz band, the 902-928 MHz band, the 2450-5800 MHz band, or the like. In some embodiments, the RFID chip is incorporated with browser-based software to increase its efficacy. In some embodiments, this software allows for different groups or specific hospital staff, nurses, and patients to see real-time data relevant to the tag, procedure, or personnel. In some embodiments, real-time data is stored and archived to make use of historical reporting functionality and to prove compliance with various industry regulations. In some embodiments, the RFID chip reports sensor data (e.g., temperature, movement, etc.). In some embodiments, the RFID chip contains or collects information that is read at a later time (after surgery). In some embodiments, information is reviewed during surgery. For example, a message may be provided to the surgeon (e.g., "the chip is just to the left of the tumor") to assist in guiding the surgeon (e.g., optimizing removal of a tumor with the appropriate margins).

In some embodiments, the tag consists of or consists essentially of the signal source and the housing or the signal source, the housing, and the RFID chip. In some embodiments, the tag (e.g., via the chip) emits an ultrasound signal (e.g., gray scale, spectral, or color Doppler) such that the signal is detectable by an ultrasound probe or a hand-held Doppler unit.

In some embodiments, a tag is heated during a procedure (e.g., via exposure to an external energy source). In some such embodiments, heating may be used to assist in coagulation or precoagulation of tissue or to provide thermotherapy (see e.g., U.S. Pat. Publ. No. 2008/0213382, herein incorporated by reference in its entirety). Heating may also be used to improve the efficacy of radiation therapy.

In some embodiments, a magnetic field and/or other sensing modality is provided by a remote activating device. In some embodiments, the remote activating device causes the activation event when in proximity (e.g., within a meter, . . . 0.5 meters, . . . 0.3 meters, . . . 0.2 meters, . . . 0.1 meters, . . . 0.05 meters, . . . , etc.) to the tag. In some embodiments, the intensity of the signal increases with closer proximity of the activating device and the tag. In some embodiments, the tag does not comprise any energy storage devices (e.g., battery, capacitor, etc.).

In some embodiments, the remote activating device employs an unmodulated constant frequency activation (i.e., the activation signal has constant amplitude and frequency). In some embodiments, the tag produces an irregularity in the activation field. The sensing method detects a shift in either amplitude or frequency induced by the tag's presence. In some embodiments, the remote activating device employs an unmodulated swept frequency (i.e., the activation signal has constant amplitude and swept frequency between two endpoints). Such devices find use with resonant-type tags such that a detectable change in the activation signal's amplitude occurs when the transmitted frequency coincides with the tag's resonant frequency.

In some embodiments, the remote activating device employs a pulsed frequency (i.e., the activation signal comprises brief excitation pulses at a periodic frequency, which may be comprised of two closely-related frequencies whose sum or difference is the response frequency of the tag). The pulsed activation produces a post-pulse sinusoidal decay signal. A tag alters the characteristic of the decaying signal, either in amplitude or time.

In some embodiments, the remote activating device comprises a hand-held component. In some embodiments, the hand-held component is lightweight to allow a surgeon to hold and manipulate the component over the course of a procedure (e.g., 5 kg or less, 4 kg or less, 3 kg or less, 2 kg or less, 1 kg or less, 0.5 kg or less, 0.25 kg or less, or any range therein between, e.g., 0.5 to 5 kg, 1 to 4 kg, etc.). In some embodiments, the hand-held component is shaped like a wand, having a proximal end that is held by the physician and a distal end that is pointed towards the treated subject or tissue harboring the tag. In some embodiments, the hand-held component is shaped like an otoscope, having a distal end that terminates at an angle (e.g., right angle) from the body of the component. In some embodiments, the remote activating device comprises an antenna that generates a magnetic field. In some embodiments, the remote activating device has only a single antenna (i.e., is monostatic). In some embodiments, the remote activating device has only two antennas (i.e., is bistatic).

In some embodiments, the magnetic field of the remote activating device is controlled by a processor running a computer program. In some embodiments, the remote activating device comprises a display or user interface that allows the user to control the remote activating device and/or monitor its functions while in use. In some embodiments, the remote activating device provides a visual, audio, numerical, symbol (e.g., arrows), textual, or other output that assists the user in locating the tag or identifying the distance to or direction of the tag from the remote activating device.

In some embodiments, the detection component comprises a series of lights (LEDs) (e.g., 5 lights) which are lit to indicate proximity, distance, or direction to the tag. In some embodiments, the user has control over the strength of the magnetic field produced by the remote activating device. In some embodiments, internal algorithms embodied in the software control the magnetic field. In some embodiments, the user may select one or more algorithms from a menu. In some embodiments, algorithms reduce or increase the sensitivity of the remote activating device based on its distance from the tag. In certain embodiments, the display on the detection component displays numerals (e.g., numbers on an LCD screen for reporting distance).

In some embodiments, an image from an imaging component is associated with data collected by the detection component. In some such embodiments, a user display provides an image of the tissue from the subject (e.g., obtained from MRI, CT, ultrasound, or other imaging modality) and overlays information about the location of the tag, the detection component, and/or a surgical tool used by the surgeon.

In some embodiments, the remote activating device comprises an excitation coil. In some embodiments, the excitation coil is provided in a patch or pad that is placed on the patient or on the operating table. In some embodiments, where the system is used to locate breast tumors, the patch encircles the treated breast or is placed otherwise near the breast. In some embodiments, a pad containing the excitation coil is placed beneath the patient. In such embodiments, a large coil or multiple coils are employed. The excitation coil(s) may comprise or consist of several turns of a flat conductor patterned on a dielectric substrate, or may comprise or consist of magnet wire wound around a suitable mandrel; the coil is powered by an external frequency source, and the magnetic field emanating from the coil penetrates the patient's body to excite the tag, whose emissions (in some embodiments at a higher harmonic of the excitation or in some temporal or spectral combination unique to the tag) are detected by the detection component.

In some embodiments, the excitation coil or coils are contained in a belt that is placed around the subject or a portion of the subject. In some embodiments, the external excitation coil may further be used for other aspects of the patient case, such as for radiotherapy. In some embodiments, the remote activating device emits light (e.g., laser light). In some embodiments, remote activating device is configured for single use (e.g., is disposable).

In some embodiments, the detection component is attached to or integrated with a surgical device, such as an electrosurgical device (e.g., electrocautery device such as a BOVIE device), cutting device, ablation device, or the like. A single housing may contain all components of the detection component and the surgical device. Alternatively, a bracket or other component is used to connect a component of a detection component to a surgical device. In some embodiments, a holder is used to mount both the electrosurgical device and the detection component together. In some embodiments, the detection component or a component thereof is attached to or integrated into another type of medical device that is used in the desired surgical procedure (e.g., clamps, endoscopes, bronchoscopes, extended bronchoscopes, dissection tools, lasers, laparoscopes, thoracoscopes, etc.).

Further provided herein are systems comprising the above tags, remote activating devices, and detection component. For example, systems may comprise the tag and detection component. Systems may further comprise other hardware (e.g., RFID reader), software, instructions, medical devices (e.g., cutting tools, imaging devices, tissue ablation devices, syringes, introduction needles/cannulas/endoscopes, sterilization components, etc.), pharmaceuticals, or other components useful, necessary, or sufficient for conducting a procedure with the tag. In some embodiments, the system comprises a computer that provides command and control functions for the tag and/or detection component. In some embodiments, the software collects and analyzes procedure data, information from an RFID chip, or other information generated during a procedure using the tag. In some embodiments, a computer comprises a display for displaying information to the treating physician, radiologist, patient, or other personnel involved in a procedure.

The tag is not limited to placement within a particular body region, body part, organ, or tissue. For example, in some embodiments, the tag is placed in the cephalic, cervical, thoracic, abdominal, pelvic, upper extremities, or lower extremities region of the body. In some embodiments, the tag is placed within an organ system, such as the skeletal system, muscular system, cardiovascular system, digestive system, endocrine system, integumentary system, urinary system, lymphatic system, immune system, respiratory system, nervous system or reproductive system. In some embodiments, the tag is placed within an organ. Such organs may include the heart, lungs, blood vessels, ligaments, tendons, salivary glands, esophagus, stomach, liver, gallbladder, pancreas, intestines, rectum, anus, hypothalamus, pituitary gland, pineal gland, thyroid, parathyroids, adrenal glands, skin, hair, fat, nails, kidneys, ureters, bladder, urethra, pharynx, larynx, bronchi, diaphragm, brain, spinal cord, peripheral nervous system, ovaries, fallopian tubes, uterus, vagina, mammary glands, testes, vas deferens, seminal vesicles, and prostate. In some embodiments, the tag is placed within tissues, such as connective, muscle, nervous, and epithelial tissues. Such tissues may include cardiac muscle tissue, skeletal muscle tissue, smooth muscle tissue, loose connective tissue, dense connective tissue, reticular connective tissue, adipose tissue, cartilage, bone, blood, fibrous connective tissue, elastic connective tissue, lymphoid connective tissue, areolar connective tissue, simple squamous epithelium, simple cuboidal epithelium, simple columnar epithelium, stratified epithelium, pseudostratified epithelium, and transitional epithelium.

In some embodiments, the tissue region where the tag is located comprises a lesion. In some embodiments, the lesion is a tumor or a tissue region identified as being at risk for forming a tumor. In some embodiments, the lesion is fibrotic tissue. In some embodiments, the lesion is an inflamed or infected region. In some embodiments, the tag may be placed within a lumen to detect function or other process of the organ or provide localizing information. For example, the tag could be swallowed, or placed into a hollow organ via endoscopy. In some embodiments, the tissue region is healthy tissue.

In some embodiments, the tag is placed within a solid tumor. Examples of solid tumors into which the tag may be placed include carcinomas, lymphomas, and sarcomas, including, but not limited to, aberrant basal-cell carcinoma, acinar cell neoplasms, acinic cell carcinoma, adenocarcinoma, adenoid cystic carcinoma, adenoid/pseudoglandular squamous cell carcinoma, adnexal neoplasms, adrenocortical adenoma, adrenocortical carcinoma, apudoma, basal cell carcinoma, basaloid squamous cell carcinoma, carcinoid, cholangiocarcinoma, cicatricial basal-cell carcinoma, clear cell adenocarcinoma, clear cell squamous-cell carcinoma, combined small cell carcinoma, comedocarcinoma, complex epithelial carcinoma, cylindroma, cystadenocarcinoma, cystadenoma, cystic basal-cell carcinoma, cystic neoplasms, ductal carcinoma, endometrioid tumor, epithelial neoplasms, extramammary Paget's disease, familial adenomatous polyposis, fibroepithelioma of Pinkus, gastrinoma, glucagonoma, Grawitz tumor, hepatocellular adenoma, hepatocellular carcinoma, hidrocystoma, Hurthle cell, infiltrative basal-cell carcinoma, insulinoma, intraepidermal squamous cell carcinoma, invasive lobular carcinoma, inverted papilloma, keratoacanthoma, Klatskin tumor, Krukenberg tumor, large cell keratinizing squamous cell carcinoma, large cell nonkeratinizing squamous cell carcinoma, linitis plastica, liposarcoma, lobular carcinoma, lymphoepithelial carcinoma, mammary ductal carcinoma, medullary carcinoma, medullary carcinoma of the breast, medullary thyroid cancer, micronodular basal-cell carcinoma, morpheaform basal-cell carcinoma, morphoeic basal-cell carcinoma, mucinous carcinoma, mucinous cystadenocarcinoma, mucinous cystadenoma, mucoepidermoid carcinoma, multiple endocrine neoplasia, neuroendocrine tumor, nodular basal-cell carcinoma, oncocytoma, osteosarcoma, ovarian serous cystadenoma, Paget's disease of the breast, pancreatic ductal carcinoma, pancreatic serous cystadenoma, papillary carcinoma, papillary hidradenoma, papillary serous cystadenocarcinoma, papillary squamous cell carcinoma, pigmented basal-cell carcinoma, polypoid basal-cell carcinoma, pore-like basal-cell carcinoma, prolactinoma, pseudomyxoma peritonei, renal cell carcinoma, renal oncocytoma, rodent ulcer, serous carcinoma, serous cystadenocarcinoma, signet ring cell carcinoma, signet-ring-cell squamous-cell carcinoma, skin appendage neoplasms, small cell carcinoma, small cell keratinizing squamous cell carcinoma, somatostatinoma, spindle cell squamous cell carcinoma, squamous cell carcinoma, squamous cell lung carcinoma, squamous cell thyroid carcinoma, superficial basal-cell carcinoma, superficial multicentric basal-cell carcinoma, syringocystadenoma papilliferum, syringoma, thymoma, transitional cell carcinoma, verrucous carcinoma, verrucous squamous cell carcinoma, VIPoma, and Warthin's tumor.

In some embodiments, placing the tag comprises the steps of inserting an introduction device into the subject and introducing the tag through the introduction device into the subject. In some embodiments, the introduction device is a needle, catheter, cannula, or endoscope. In some embodiments, the tag is forced through the introduction device (e.g., via physical force, pressure, or any other suitable technique) and released into the subject at the distal end of the introduction device. After the tag is placed, the introduction device is withdrawn, leaving the tag at the desired location with the subject. In some embodiments, the introduction of the tag is guided by imaging technology.

In some embodiments, multiple tags are placed into the subject. The tags may be of identical type or may differ (e.g., differ in signal type). The tags may be placed in proximity to one another or at distant locations. Multiple tags are used, in some embodiments, to triangulate the location intended for medical intervention.

In some embodiments, the tags are further used as fiducials for radiotherapy (or other targeted therapy). The location of the tags is identified with an external reader and used to place, for example, laser light on the skin surface exactly where the chip is located. This eliminates the need to use X-ray, CT, or fluoroscopy to see the locations of the fiducials. This also decreases or eliminates the need to put skin markers (e.g., tattoos) on patients. This also helps in respiratory compensation as the fiducial moves up and down with a tumor in the lung or abdomen. Therefore, one can conduct real-time radiation only when the tumor is in the correct position and decrease damage to the background tissue (e.g., avoid burning a vertical stripe in the patient as the tumor moves up and down). The use as fiducials for director therapy (e.g., radiation therapy) also all enhances triangulation as depth information (based on signal strength) assists in localization of the tumor to minimize collateral damage.

In certain embodiments, a fiduciary or localizing system is placed during an endoscopic procedure. For example, during colonoscopy, gastroscopy, duodenoscopy, cystoscopy, etc., a fiducial could be attached to a polyp or other mass. This fiducial is then localized during a subsequent procedure such as, for example, a laparoscopic colon resection or other procedure.

In some embodiments, the tag comprises a fixing component on the outer surface (e.g., of the housing, if present) to anchor the tag in the desired location. In some embodiments, the fixing component is a hook, barb, or other physical extension. In some embodiments, the fixing component is deployable upon placement. In some embodiments, the fixing component is a textured surface. In some embodiments, the fixing component is an adhesive.

It will be appreciated that the systems and methods described herein may be applied to other uses, including non-medical uses. The technology finds use in any situation where localization of a tag is desired, including, but not limited to, surgical procedures, diagnostic procedures, veterinary procedures, food analysis, industrial applications, and environmental applications.

Definitions

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), optical discs, and magnetic tape. In certain embodiments, the computer memory and computer processor are part of a non-transitory computer (e.g., in the control unit). In certain embodiments, non-transitory computer readable media is employed, where non-transitory computer-readable media comprises all computer-readable media with the sole exception being a transitory, propagating signal.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks, whether local or distant (e.g., cloud-based).

As used herein, the term "in electronic communication" refers to electrical devices (e.g., computers, processors, etc.) that are configured to communicate with one another through direct or indirect signaling. For example, a conference bridge that is connected to a processor through a cable or wire, such that information can pass between the conference bridge and the processor, are in electronic communication with one another. Likewise, a computer configured to transmit (e.g., through cables, wires, infrared signals, telephone lines, airwaves, etc.) information to another computer or device, is in electronic communication with the other computer or device.

As used herein, the term "transmitting" refers to the movement of information (e.g., data) from one location to another (e.g., from one device to another) using any suitable means.

As used herein, the term "subject" or "patient" refers to any animal (e.g., a mammal), including, but not limited to, humans, non-human primates, companion animals, livestock, equines, rodents, and the like, which is to be the recipient of a particular treatment. Typically, the terms "subject" and "patient" are used interchangeably herein in reference to a human subject.

As used herein, the term "subject/patient suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the stage of cancer is not known. The term further includes people who once had cancer (e.g., an individual in remission).

As used herein, the term "biopsy tissue" refers to a sample of tissue (e.g., breast tissue) that is removed from a subject for the purpose of determining if the sample contains cancerous tissue. In some embodiment, biopsy tissue is obtained because a subject is suspected of having cancer. The biopsy tissue is then examined (e.g., by microscopy; by molecular testing) for the presence or absence of cancer.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include tissue, blood products, such as plasma, serum and the like. Such examples are not however to be construed as limiting the sample types applicable to the present invention.

DETAILED DESCRIPTION

Provided herein are systems, devices, assemblies, and methods for localization a tag in a tissue of a patient. For example, provided herein are systems, devices, and methods employing a detection component that is attached to or integrated with a surgical device, where the detection component can detect a signal from a tag in a patient, where the tag is activated by remote introduction of a magnetic field. In certain embodiments, the detection component comprises three sense coils arranged in a triangle.

Systems and Devices

Figure 1A:
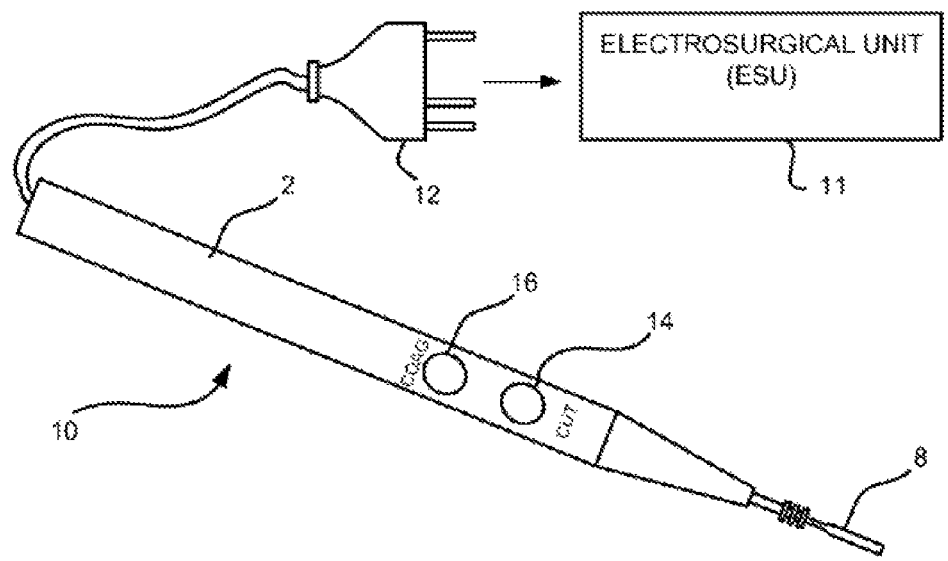
FIG. 1A shows an exemplary medical device (electrocautery device) from U.S. Pat. No. 8,998,899, which is herein incorporated by reference.
Figure 1B:
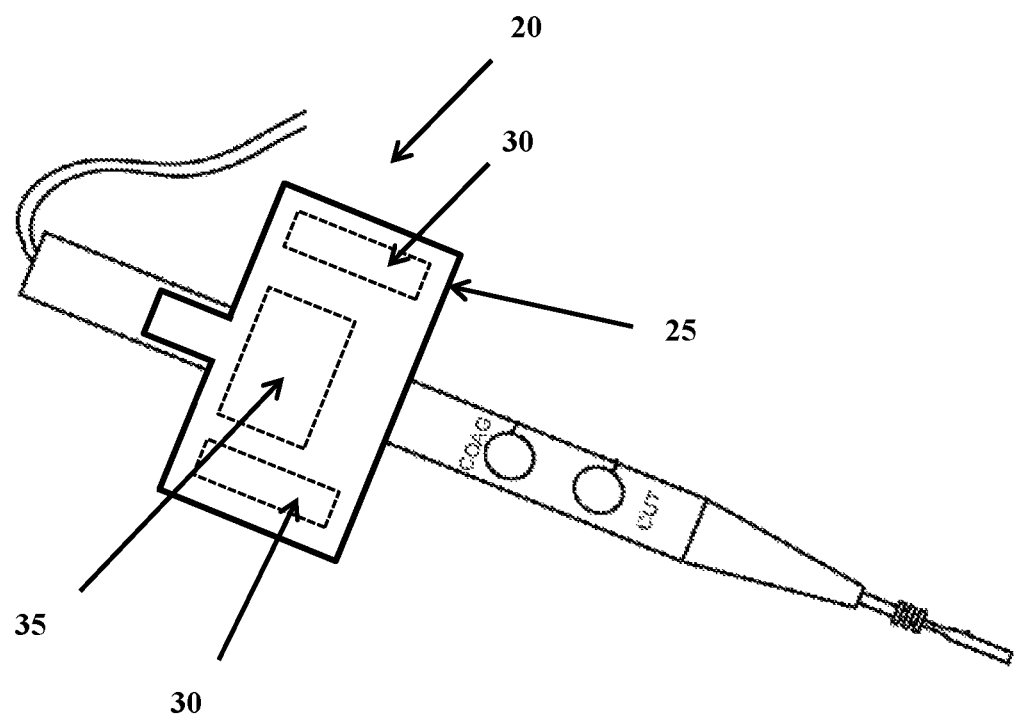
FIG. 1B shows an exemplary device/assembly of the present disclosure, showing a detection component attached to the medical device of FIG. 1A.

FIG. 1A shows an exemplary medical device (electrocautery device) from U.S. Pat. No. 8,998,899, which is herein incorporated by reference in its entirety. Specifically, FIG. 1B shows a surgical instrument (10), with a housing (2) having a coagulation button (16) and a cut mode button (14). The tip of the surgical instrument (10) is attached to electrode (8), that may be used for cutting and/or cauterizing tissue. The surgical device (10) is attached to an electrical surgical unit (11) via connector (12). The electrical surgical unit (11) provides power and various controls. FIG. 1B shows an exemplary device/assembly of the present disclosure, showing a detection component (20) attached to the medical device of FIG. 1A. The detection component (20) is shown with two sense coils (30) inside housing (25). Also inside the house (25) is electronics component (35) which may, for example, be used to process the signals received by sense coils (30), and/or provide a display to a user regarding distance to a tag embedded in a patient.

Figure 2:
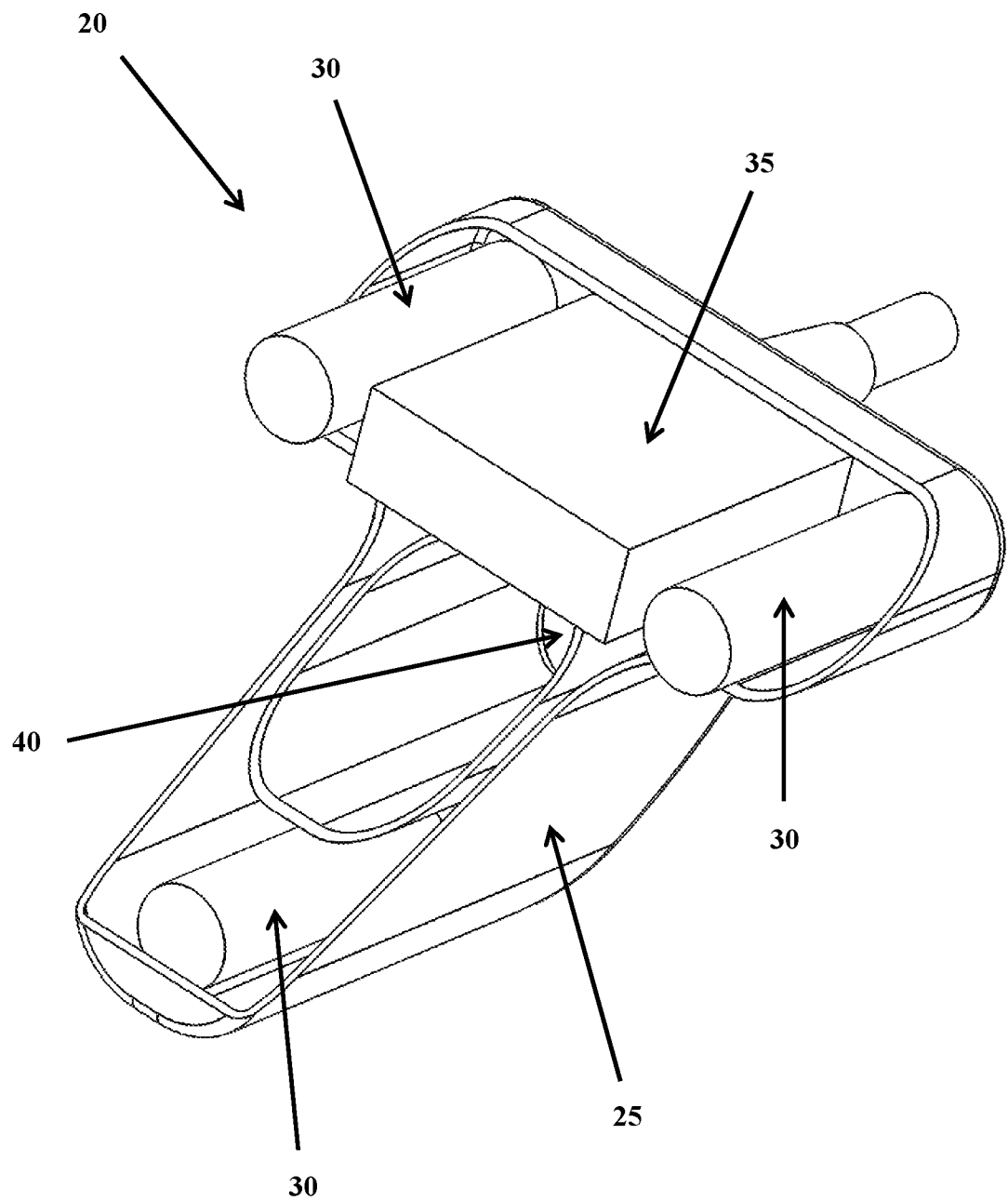
FIG. 2 shows an exemplary detection component (20) having a detection component housing (25) which contains three sense coils (30) and an electronics component (35). The housing (25) also has a device-securing opening (40) therein.

FIG. 2 shows an exemplary detection component (20) having a detection component housing (25) (e.g., composed of plastic or other material) which contains three sense coils (30) (which are arranged in a triangle configuration) and an electronics component (35). The housing (25) also has a device-securing opening (40) therein, which allows a medical device to be inserted and secured in place.

Figure 3:
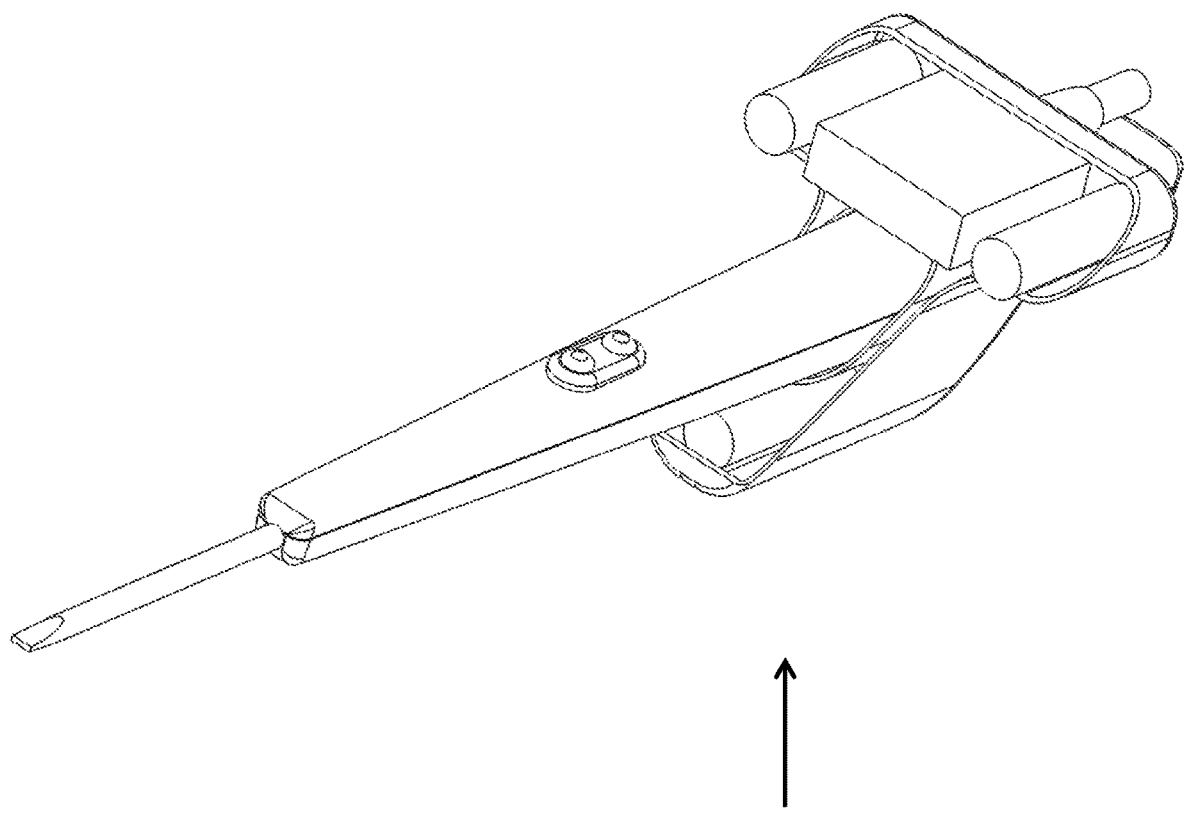
FIG. 3 shows an exemplary detection component—medical device assembly (21), wherein the surgical device is inserted through the device-securing opening of the detection component housing.

FIG. 3 shows an exemplary detection component—medical device assembly (21), wherein the surgical device is inserted through the device-securing opening of the detection component housing. In this assembly, for example, the detection component is positioned such that it does not interfere with a user (e.g., surgeon) using the medical device in its normal mode of use. In this figure, the detection component is position distal to the cutting and/or cauterizing end of the medical device, and away from the buttons used during operation.

Figure 4:
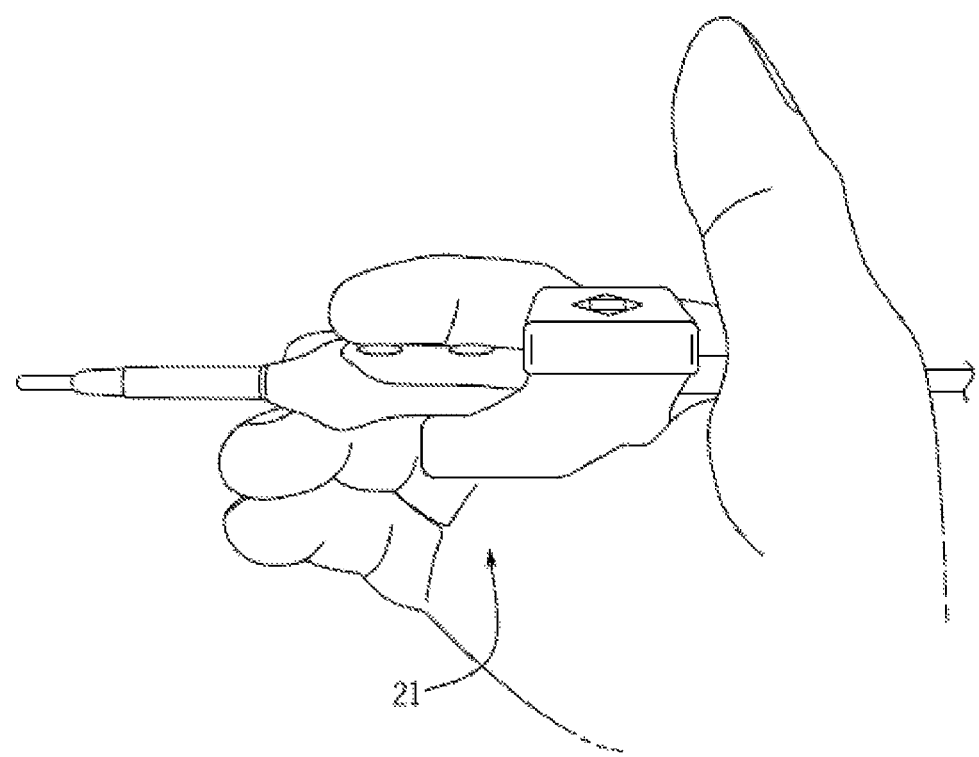
FIG. 4 shown a photograph of an exemplary detection component—medical device assembly.

FIG. 4 shown a photograph of an exemplary detection component-medical device assembly in the hand of a user. Again, the detection component is positioned such that the user is free to use the device and operate the buttons and cutting/cauterizing tip in a normal fashion.

Figure 5:
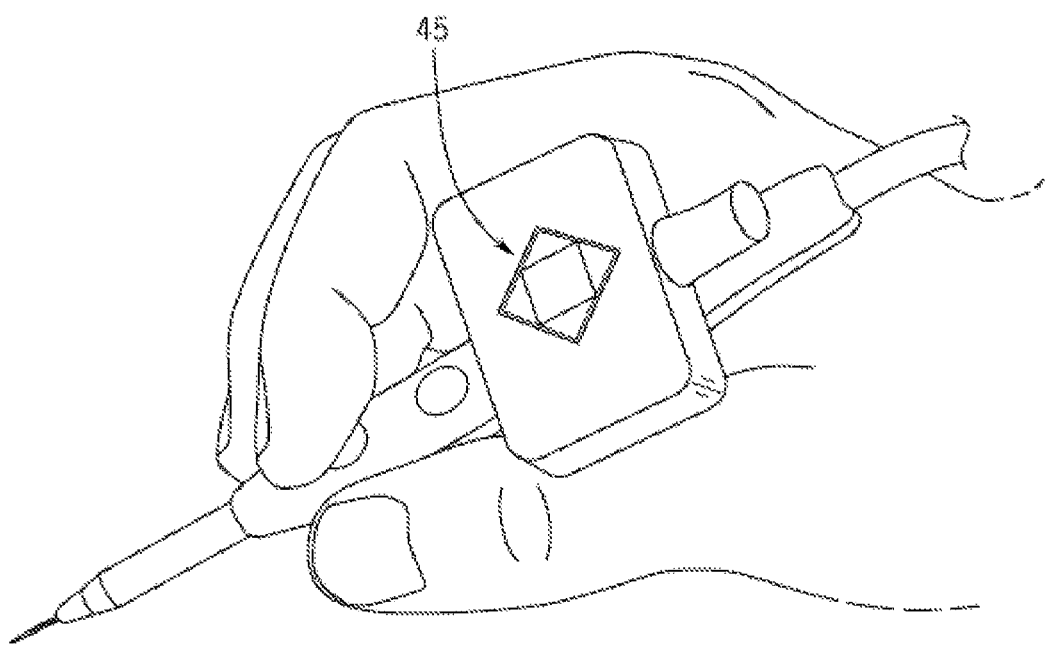
FIG. 5 shows a photograph of an exemplary detection component with a visual display (45) located therein.

FIG. 5 shows a photograph of an exemplary detection component with a visual display (45) located therein. A visual display may be used to inform the user (e.g., a surgeon) how far the tag (in the patient) is from the device, and may also be used to help keep the surgical device oriented in the correct planes (e.g., to avoid unnecessary cutting or cauterizing with the medical device). In certain embodiments, orientation and/or distance are indicated with a number of lights (e.g., 5 LED lights).

Figure 6:
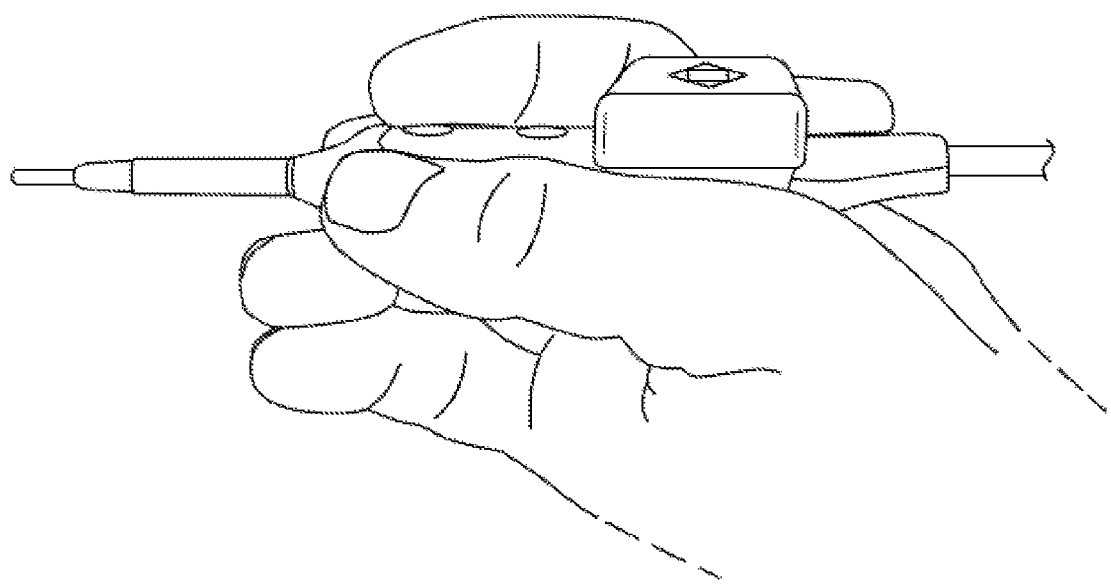
FIG. 6 shows a photograph of a side view of an exemplary detection component—medical device assembly.

FIG. 6 shows a photograph of a side view of an exemplary detection component—medical device assembly.

Figure 7:
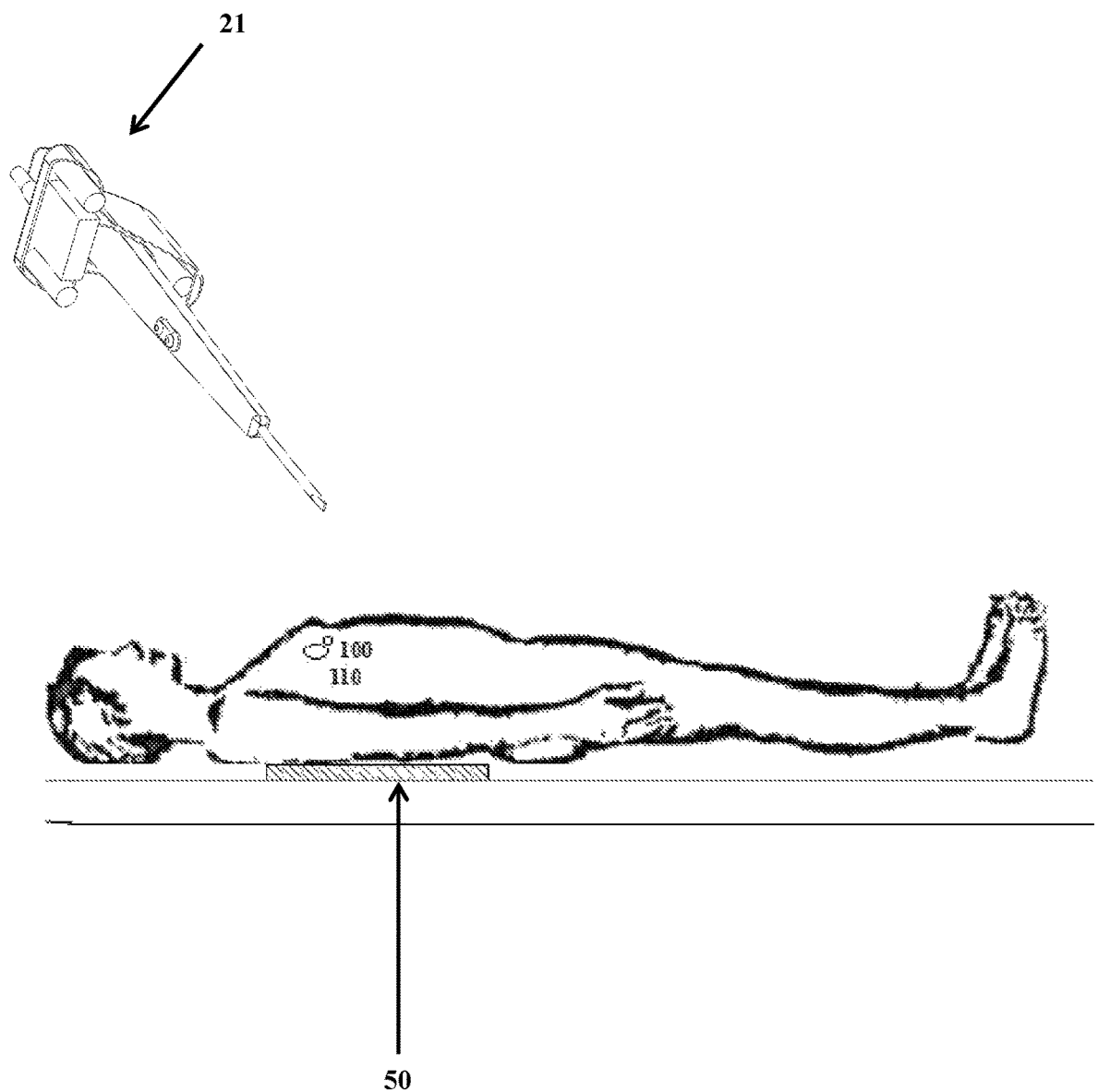
FIG. 7, which is not to scale, shows a patient with a tag (100) inserted next to a solid tumor (110), wherein the patient is laying on top of a remote activating device (50). Also shown is a detection component-surgical device assembly (21).

FIG. 7 shows a patient with a tag (100) inserted next to a solid tumor (110) (e.g., in breast tissue of the patient), wherein the patient is laying on top of a remote activating device (50), which is shown as a flat pad. Also shown is a detection component-surgical device assembly (21). The remote activating device may also be positioned closer to the tag (100) (e.g., by being placed on the abdomen), or placed further away (e.g., under the table or mattress the patient is supported on). In certain embodiments, the remote activating device (50) generates a magnetic field that passed through the patient's body, striking the tag, which causes a reflection or irregularity in the magnetic field. Such reflection or irregularity is detected by the detection component. A visual display (e.g., on the detection component or elsewhere) then reports the distance of the medical device tip (e.g., cutting and/or cautery tip) allowing the user (e.g., a surgeon) to precisely guide the medical device tip to the tumor. In certain embodiments, prior to any cutting of tissue, the detection component—medical device (21) is moved all around the outside of the patient near the tag in order to calibrate the detection component.

Figure 8:
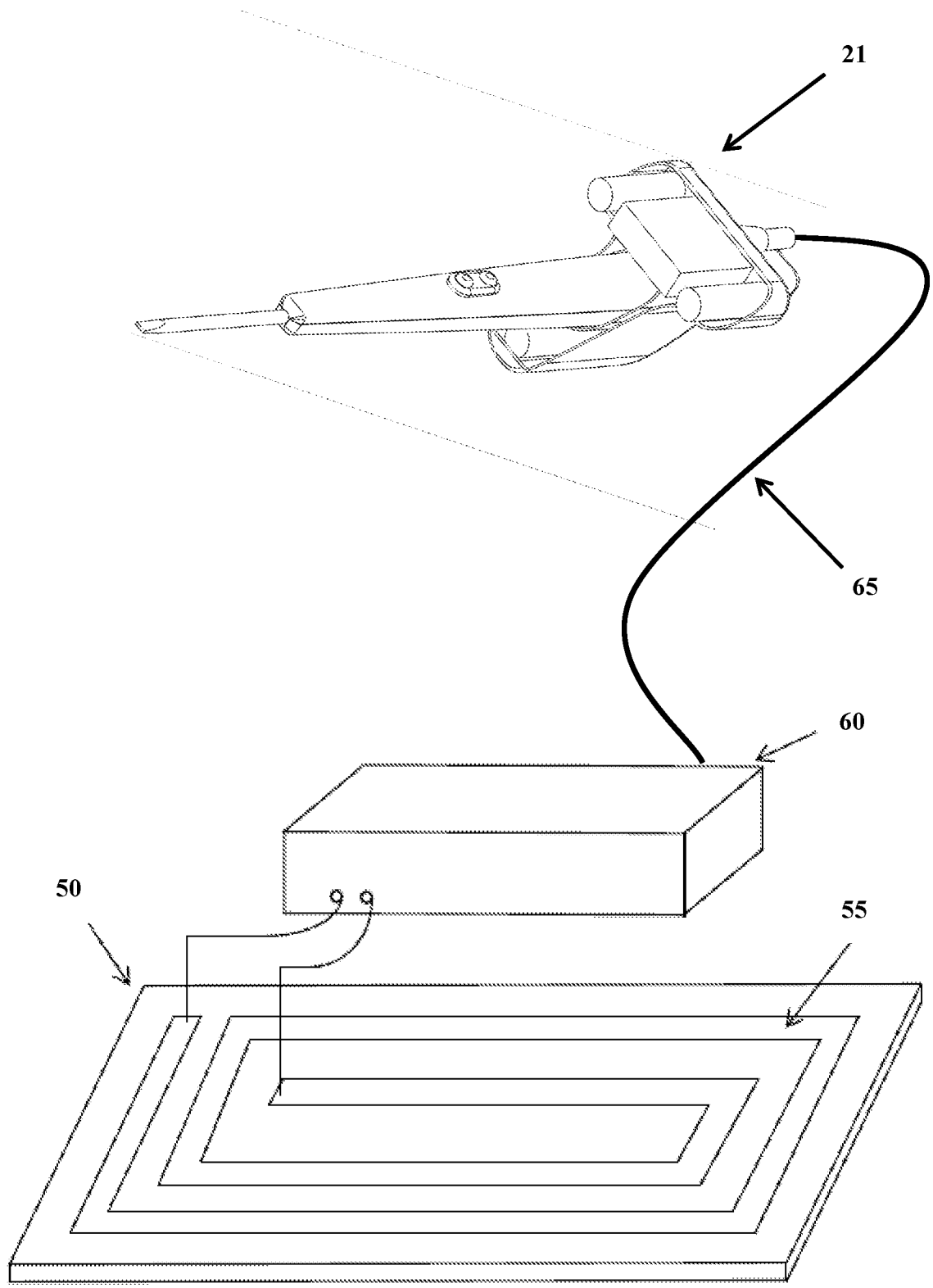
FIG. 8 shows a control unit (60) that is attached to both a remote activating device (50) and a detection component-medical device assembly (21). The remote activating device (50) has an excitation coil (55). The detection component—surgical device assembly (21) is attached to the control unit (60) via connection wire (65).

FIG. 8 shows a control unit (60) that is attached to both a remote activating device (50) and a detection component-medical device assembly (21). The remote activating device (50) has an excitation coil (55). The detection component—surgical device assembly (21) is attached to the control unit (60) via connection wire (65). In certain embodiments, when the power of the medical device is activated (e.g., to cut or cauterize) the control unit turns off the magnetic field from the remote activating device, and then turns the magnetic field back on when the power is not activated on the medical device. In this regard, any magnetic field generated by the medical device itself does not disturb the magnetic field generated by the remote activating device and vice versa. This help prevent the detection component from picking up false signals (from the medical device) that are not related to the location of the tag in the patient.

Tag Placement

The technology is not limited by the mode of tag placement and a wide variety of placements techniques are contemplated including, but not limited to, open surgery, laparoscopy, endoscopy, via endovascular catheter, etc. The tags may be placed by any suitable device, including, but not limited to, syringes, endoscopes, bronchoscopes, extended bronchoscopes, laparoscopes, thoracoscopes, etc. An exemplary protocol is provided below.

A patient previously identified as having a breast tumor is admitted to a medical facility. The patient is initially sent to radiology. The radiologist examines prior imaging information identifying the target tumor. The subject is administered a local anesthetic, usually lidocaine or a derivative, using a needle introduced percutaneously. The subject is positioned in an imaging device, generally either ultrasound, conventional mammography, or a stereotactic unit. The location of the tumor is determined. An introducer needle (usually 6-20 gauge) is inserted either into or just proximal to the tumor and a biopsy needle is placed through the introducer needle and a specimen is obtained using a variety of methods (suction, mechanical cutting, freezing to fix the position of the tissue followed by mechanical cutting). After the specimen is obtained and sent for pathologic examination, a 6-20 gauge tag delivery needle is inserted into the coaxial introducer needle to the tissue with the distal open end positioned at the lesion. A tag is inserted into the proximal end of the delivery needle and delivered by plunger through the opening at the distal end of the needle and into the tissue. Likewise, the tag could have been pre-positioned at the distal end of the delivery needle. Proper location of the tag is confirmed via imaging. The delivery needle is withdrawn, leaving the tag in place in the breast tissue.

This type of procedure can be performed in an analogous manner in virtually any body space, organ, or pathologic tissue with the intent of localizing that tissue or space for further diagnosis or treatment of any kind. Areas of particular interest include but are not limited to the following organs, and disease processes that take place within them: brain, skull, head and neck, thoracic cavity, lungs, heart, blood vessels, gastrointestinal structures, liver, spleen, pancreas, kidneys, retroperitoneum, lymph nodes, pelvis, bladder, genitourinary system, uterus, ovaries, and nerves.

Surgical Procedure

The patient is placed onto an operating table with the surgical area exposed and sterilized. The surgeon is provided with the imaging information showing the location of the tumor and tag. An incision is made at the location of the entry point of the placement needle. The remote activating device is placed in proximity to the tissue to activate the tag. The detection component detects a signal from the tag and allow the surgeon to guide the direction medical device toward the tumor. Once the tumor is localized, the surgeon removes the appropriate tissue and removes the tag.

Use of this system and procedure significantly reduces procedure cost, time, and patient inconvenience as compared to wire placement and other unguided surgeries. Use of the tag reduces the number of imaging steps required and reduces time spent in radiology and surgery. Further, the patient is not left waiting for surgery with a wire hanging out of their body. Avoidance of the wire further reduces pain or discomfort associated with the pulling on the wire.

In certain embodiments, the detection component is moved around the outside of the patient, sensing the tag at many different positions to build a 3D image of the location of tag within the tissue of the patient. Such data regarding the scan can, for example, be stored in the detection component or control unit and then used during a surgical procedure to determine the optimal point of entry into the patient's tissue, as well as the angle or angles which are best suited to approach the tag, and ultimately the associated tumor (e.g., to minimize cutting of non-target tissue and to maximize the removal of the tumor or tumors associated with the tag). Such 3D image scanning (e.g., prior to surgery) helps achieve the best result for the patient and helps reduce the need for repeating the procedure (e.g., to come back for parts of the tumor that were missed on the initial surgery).

In some embodiments, the 3D image generated by moving the detection component around the location of a tag in a patient is combined with an another image of the patient with the tag (e.g., generated by MRI, CT, etc.) to generate an image fusion. Combining two or more images of a patient using fiducials as marker points has been described previously (e.g., see, U.S. Pat. No. 7,848,553, and U.S. Pat. Pub. 20030153850, both of which are herein incorporated by reference in their entireties). Commercial image fusion systems include STEALTHSTATION system and PATHFINDER system. Generating image fusions using the detection component described herein (e.g., where at least one or two implanted tags are used as fiducial points of reference), and then using the detection device for a procedure on a patient with the tags still in place, allows for real-time location correction for any movement of the patient (e.g., via breathing, changed position, organ movement during a packing procedure, etc.). In this regard, in some embodiments, the detection components herein, and their guidance system (e.g., audible, tactile, or visuals signals) is corrected during a surgical procedure (e.g., in real-time) so the operator is guided appropriately based on any changes in the patient tissue position (e.g., position of a tumor). The tag or tags serve as the fiducial points of reference for both the 3D image generated by the detection component, as well as the secondary image (e.g., from an MRI or CT image). The tags also then serve as fiducial points of reference during the procedure to orient the detection device and account for changes in position of the patient. In some embodiments, the fiducials are implanted in a subject (e.g., in breast tissue) or be external (e.g., such as placed on each earlobe prior to brain scans and subsequent brain surgery using the detection component and corresponding surgical device). To see the position, in some embodiments, the tag is used in combination with one or more other fiducials. For example, one tag in the breast and a sticker containing a fiducial on each shoulder. This type of real-time use of image fusion and location information may be used in any type of suitable surgical or ablative procedure, including for example, neurosurgery, hepatobiliary surgery, gynecological surgery, ENT surgery, urological surgery, etc.

In certain embodiments, images (e.g., MRI, CT, etc.) that are generated for use with the detection component (and corresponding surgical device) are marked to indicate the location of a target tumor, including a surgical margin around the tumor to ensure complete removal. In some embodiments, a predetermined margin such as 0.5 . . . 1 cm . . . 1.5 cm . . . 2 cm etc., is set around a tumor to ensure removal. The surgical margin around a tumor could be set as a sphere, or drawn to correspond to any irregular shape of the tumor (e.g., hand drawn by a doctor on an image to match any irregular shape). In some embodiments, this surgical margin around a tumor is used such that, prior to using the detection component device and corresponding surgical device, one could calibrate for the signal intensity in the x, y and z axis related to this surgical margin such that whenever the device reaches a user defined boundary (the predetermined distance from the tumor) something changes, such as an audible, visual, or tactile signal (e.g., a yellow light when a user is at the surgical margin around tumor, and red light when the surgical device has gone within the predetermined surgical margin). In certain embodiments, there could be a signal warning that the surgical device is too close to the surgical margin (e.g., 5 mm), such as a red warning signal.

In certain embodiments, the tag is placed at or near the tip of the surgical instrument or device to track its location (e.g., whether fused with a medical image or not). For example, the tag could be placed on or near the tip of a nasogastric tube or bladder catheter to confirm the tip position from outside the patient. Such embodiments, may be used to improve safety of surgical procedures. Also, in some embodiments, the tag is placed on or near the tip of a vascular catheter, and the position of the catheter fused to a medical image (CT or MRI) to give the location of the instrument in the human body. Likewise for any surgical instrument, catheter, endoscopic instrument, sensing device, biopsy needle, or anything else inserted into the human body where the tip location is important, a tag may be used near or at the tip of such devices. In certain embodiments, such as for simple applications, these could be unfused and the location determined from outside the body by a reader, or in the case of complicated anatomy, the location could be superimposed on a calibrated image set.

In certain embodiments, the detector component comprises one or more lasers that are directed onto (e.g. projected onto) the surgical/procedure field (e.g., internal tissue of a patient) as a guide to a the user (e.g., as a guide to the target tumor that is to be resected). In certain embodiments, multiple lasers are used (e.g., all the same color or providing different colors). Such laser projection onto the surgical/procedure field allows the user (e.g., physician) to be guided to the target (e.g., tumor) without the need to look away from the surgical or procedure field. In certain embodiments, the detection component is attached to a curved partially reflective lens that is, for example, be flipped up for easy viewing of the laser lights on the surgical field. Such a lens reflects the guiding lights towards the operator regardless of the orientation of the physician's head and the instrument surface. Such lens, in some embodiments, are used to decrease parallax, and improve the viewing angle for the physician.

In certain embodiments, the display for the detection component is not part of or attached to the detection component, and instead is remote. For example, the display component may be part of a head mounted, such as Google GLASS or similar devices that present a display close to a user's eye or eyes. In this regard, there may be a wireless connection between the detection component and the display, such as a BLUETOOTH connection.

We claim:

1. A system comprising:
   i) a remote activating device that generates a magnetic field, wherein said remote activating device comprises a pad configured to be positioned: i) on or under said patient, or ii) on or under a table or bed said patient is on, wherein said pad comprises multiple activating coils,
   ii) a tag that is insertable at a location in or on a tissue of a patient, wherein said tag is activated by said magnetic field,
   iii) a control unit comprising a processor and a control software, wherein said control unit is linked to said remote activating device, and
   iv) a display component configured to provide distance of said tag to a hand-held surgical instrument, wherein said display component is removably mounted to said hand-held surgical instrument.

2. The system of claim 1, wherein said tag comprises an RFID tag.

3. The system of claim 1, wherein each of said activating coils comprises magnet wire wound around a mandrel.

4. A method for localizing a tissue region of a patient, comprising:
   a) placing a remote activating device and a patient in proximity to each other, wherein said remote activating device comprises a pad with multiple activating coils that generate a magnetic field, and
   wherein said patient comprises a tag at a location in, on, or proximal to a tissue of said patient;
   b) positioning a hand-held surgical instrument in proximity to said tissue of said patient such that said patient is between said hand-held surgical instrument and said pad;
   c) localizing said tag in said patient by generating a magnetic field with said remote activating device and detecting a signal from said tag; and
   d) displaying, on a display component, the distance of said tag to said hand-held surgical instrument, wherein said display component is removably mounted to said hand-held surgical instrument.

5. The method of claim 4, wherein said tag comprises an RFID tag.

6. The method of claim 4, wherein each of said activating coils comprises magnet wire wound around a mandrel.

* * * * *